United States Patent
Wuest

(10) Patent No.: US 9,439,701 B2
(45) Date of Patent: Sep. 13, 2016

(54) SHAPING TOOL FOR SHAPING AN ACETABULUM

(75) Inventor: Edgar Wuest, Gross-Umstadt (DE)

(73) Assignee: Heraeus Medical GmbH, Wehrheim (DE)

( * ) Notice: Subject to any disclaimer, the term of this patent is extended or adjusted under 35 U.S.C. 154(b) by 233 days.

(21) Appl. No.: 13/882,660

(22) PCT Filed: Nov. 23, 2011

(86) PCT No.: PCT/EP2011/005893
§ 371 (c)(1),
(2), (4) Date: Apr. 30, 2013

(87) PCT Pub. No.: WO2012/079695
PCT Pub. Date: Jun. 21, 2012

(65) Prior Publication Data
US 2013/0253523 A1 Sep. 26, 2013

Related U.S. Application Data

(60) Provisional application No. 61/491,599, filed on May 31, 2011.

(30) Foreign Application Priority Data

Dec. 15, 2010 (DE) ........................ 10 2010 054 663

(51) Int. Cl.
*A61B 17/88* (2006.01)
*A61F 2/46* (2006.01)
(52) U.S. Cl.
CPC .... *A61B 17/8802* (2013.01); *A61F 2002/4631* (2013.01)

(58) Field of Classification Search
CPC ............ A61B 17/92; A61B 2017/922; A61B 2017/924; A61F 2/4601; A61F 2/46; A61F 2/4609; A61F 2002/4624
USPC .................................................... 606/99, 100
See application file for complete search history.

(56) References Cited

U.S. PATENT DOCUMENTS

| 5,658,338 | A | * | 8/1997 | Tullos et al. | ............... 623/22.39 |
| 6,019,766 | A | | 2/2000 | Ling et al. | |
| 2007/0123985 | A1 | * | 5/2007 | Errico et al. | ............... 623/17.11 |

FOREIGN PATENT DOCUMENTS

| EP | 0916324 A2 | 5/1999 |
| GB | 2297911 A | 8/1996 |
| WO | 2006024840 A1 | 3/2006 |

OTHER PUBLICATIONS

International Search Report for Application No. PCT/EP2011/005893 dated Mar. 5, 2012.
Written Opinion of the International Searching Authority for Application No. PCT/EP2011/005893 dated Mar. 5, 2012.

* cited by examiner

*Primary Examiner* — Anu Ramana
(74) *Attorney, Agent, or Firm* — Norris McLaughlin & Marcus, P.A.

(57) ABSTRACT

A shaping tool shapes a smooth bone cement surface, in particular for implantation of an artificial acetabulum. The shaping tool has a curvature, whereby the shaping tool has a curved base body and at least two layers, whereby a first layer covers the curvature of the base body at least in part and is connected to the base body in a detachable manner, and a second layer covers the first layer at least in part and is connected to the first layer in a detachable manner. The shaping tool is usable to pre-shape a bone cement for insertion of an artificial acetabulum.

18 Claims, 3 Drawing Sheets

SHAPING TOOL FOR SHAPING AN ACETABULUM

Figure 1:
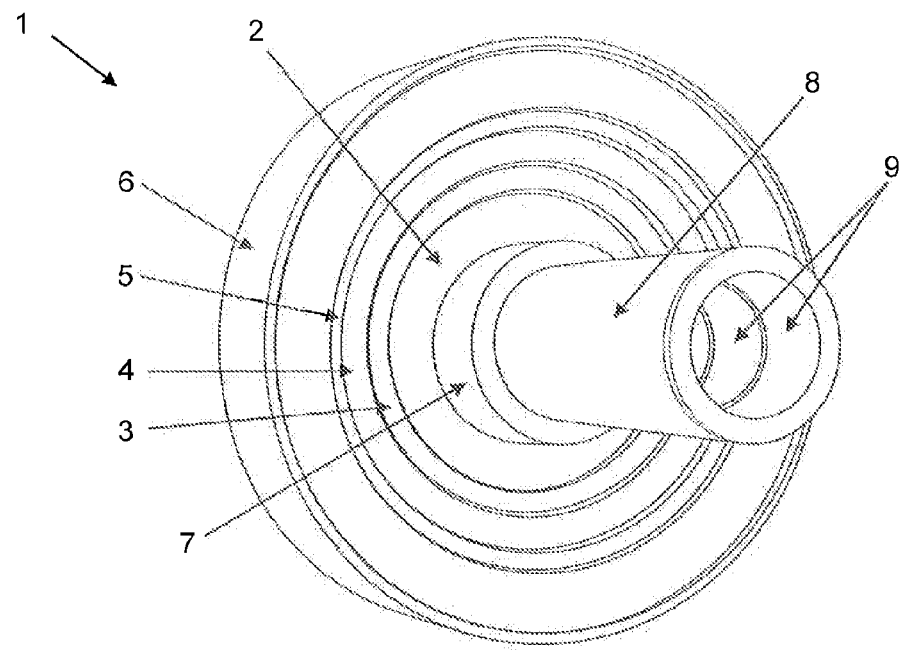

This is a 371 of PCT/EP2011/005893 filed 23 Nov. 2011 (international filing date), and claims the priority of German Application No. 10 210 054 663.1 filed 15 Dec. 2010 and U.S. Application No. 61/491,599 filed 31 May 2011.

The invention relates to a shaping tool for shaping a smooth cement surface, in particular for implantation of an artificial acetabulum, comprising a curvature.

Inserting an artificial acetabulum for replacement of an artificial hip joint involves that the artificial acetabulum, which usually consists of an alloy, such as, for example, a chromium-cobalt-molybdenum alloy, is anchored in the patient's hip through the use of a medical cement. For this purpose, the bone cement is first pressed into the cancellous bone of the acetabulum. Subsequently, a semi-spherical cement layer of even thickness must be produced for anchoring of the artificial acetabulum.

In order to generate a compact and firm connection, it is advantageous to press the bone cement into a recess in the hip bone. From GB 2 297 911 A is known a shaping tool for generating a spherical, thin cement layer (called "acetabular pressurizer") in which a compressing piston is pressed onto a flexible membrane in order to press a bone cement into a depression in a hip bone. Through this means, a spherical shape is produced in the cement into which the artificial acetabulum can be inserted.

The diameter of the spherical shape in the bone cement must match the shape of the artificial acetabulum. If the diameter of the bone cement impression fails to match the artificial acetabulum to a sufficient degree, the connection of the bone cement to the artificial acetabulum and thus the anchoring of the artificial acetabulum in the pelvis of the patient may be weakened.

Manufacturers of hip prostheses include shaping tools of this type, "acetabular pressurizer", in their product portfolio. Said tools are supplied individually for the respective acetabular diameters as single-use product or designed for re-sterilisation and thus re-use. For this purpose, manufacturers supply a handle onto which the corresponding shaping tool needs to be attached. Usually, the handle needs to be sterilised prior to the operation. The hospital needs to keep a stock of shaping tools of all possible sizes, which usually are available as 5-packs or 10-packs of various sizes.

This is disadvantageous in that the proper size needs to be selected and provided during the operation. If applicable, the handle and the shaping tool itself may need to be sterilised in order to render the shaping tool ready for use. A large variety of shapes needs to be kept in stock at all times to always have the proper size available. This may interfere with and cause delays in the critical period of time in the often hectic process of an operation.

Accordingly, it is the object of the invention to overcome the disadvantages of the prior art. In particular, the invention is to provide an easy-to-use shaping tool for shaping a bone cement layer for anchoring of an artificial acetabulum in pelvic bone, whereby the shaping tool is easy and simple to operate and interferes as little as possible with the process of an operation involving the insertion of an artificial hip joint. In this context, the ease of use shall not adversely affect the quality of the connection of the artificial acetabulum to the pelvic bone, but rather enable a connection that is as solid as possible.

The object of the invention is met in that the shaping tool has a curved base body and at least two layers, whereby a first layer covers the curvature of the base body at least in part and is connected to the base body in a detachable manner, and a second layer covers the first layer at least in part and is connected to the first layer in a detachable manner.

In this context, the shaping tool can be provided to comprise three to forty layers, preferably five to thirty, particularly preferably eight to twenty layers, which cover each other, at least in part, in the manner of onion skins, and are connected to each other in a detachable manner.

The invention can further provide the curvature of the base body and layers to be spherical.

In this context, the invention can provide the curvature of the base body and layers to correspond to a spherical segment, preferably a spherical segment at a third of the diameter of the sphere.

An advantageous refinement of the invention provides the shaping tool to comprise a handle or an adapter, preferably a cylindrical handle or adapter.

In this context, the invention can provide the adapter to be a tube, in particular a tube that tapers on its inside in one direction and into which a cement cartridge or the attachment of a cement cartridge for medical cements can be plugged.

In this context, the invention can further provide the tube-shaped adapter to taper in discrete steps.

Shaping tools having a handle or adapter can be provided such that the adapter or the handle can be plugged into the base body, preferably into a depression in the base body and/or a sleeve that is arranged on the base body.

In order to be able to produce a cement shape for hip joint prostheses, the invention can provide the curvature of the base body to have a diameter of 35 to 50 mm, preferably of 40 to 48 mm, particularly preferably of 45 mm.

The invention can also provide the thickness of the layers to be between 0.5 and 15 mm, preferably between 1 and 10 mm, particularly preferably between 2 and 7 mm.

For easier operation of the shaping tool, the invention can provide a tongue to be arranged on each layer that allows the corresponding layer along with all layers arranged above it to be manually detachable from the layers arranged below it or from the base body, in particular by pulling it off or lifting it off.

In this context, the invention can provide the tongues to be arranged on the edge of the layers.

Moreover, the invention can provide the layers to be connected to the base body and to each other in a manually detachable manner.

In order to ensure that the operation of the shaping tool is rapid and intuitive, the invention can provide a labelling to be arranged on at least one of the layers, in particular on the tongues of the layers and preferably on the base body also, which labelling allows the size, in particular the diameter, of the curvature to be read such that a certain size of an artificial acetabulum can be allocated to each layer.

For this purpose, the invention can also provide the layers to be transparent or coloured, preferably to be coloured differently.

A particularly advantageous refinement of the invention provides the layers to be situated in a positive fit within each other and on the base body.

The invention can also provide the base body to be made of a hard material, preferably a plastic material.

Moreover, the invention can provide the layers to consist of a hard material, preferably a plastic material, or of a soft material, in particular silicone.

For medical application, it can be particularly advantageous for the shaping tool to be packaged and/or sterilised in a suitable package for sterilisation, preferably through gamma radiation sterilisation or exposure to gas, in particular ethylene oxide. The sterile or sterilisable package allows the shaping tool to be used rapidly or to be prepared and then stored for later rapid use during an operation.

The invention can further provide for the curved surface of the base body and layers to be smooth.

In order to ensure that any sterilisation by steam would be inappropriate and non-complete, the invention can provide the materials of which the base body and/or the layers is made to be destructible upon exposure to steam.

And lastly, the invention can provide the materials of which the base body and/or layers consist to not undergo any chemical reaction with bone cement.

The invention is based on the surprising insight according to which the layered structure of the shaping tool allows a variable shaping tool to be provided that can be adapted to the size of the corresponding artificial acetabulum. The layers with a diameter that is too large for the artificial acetabulum to be inserted can simply be pulled off or torn off and removed.

The rationale underlying the invention is to provide just a single shaping tool, or "pressurizer", that covers all common acetabular diameters. The invention is advantageous in that only a single product covering all acetabular sizes needs to be kept in stock. Moreover, a refinement of the invention having an adapter allows to dispense with the handle, which is usually needed. The shaping tool, or "pressurizer", can in this case be plugged onto the majority of the commercial bone cement mixing systems, which use, in particular, an application spout.

The shaping tool according to the invention is used in the cementing of an acetabulum. Here, the cement is pressed under pressure into the cancellous acetabular bone that has previously been exposed through the use of a milling machine. The invention enables improved integration of cement and bone and a more homogeneous cement jacket to be formed under the acetabulum to be implanted.

The adapter allows the cartridge, which was just used during the operation, to be used as a handle for the shaping tool. For this purpose, the cartridge simply needs to be plugged into the adapter. For this purpose, the dispensing tube of the cartridge or the cartridge itself are plugged into a tube-shaped adapter that tapers on its inside, until the cartridge is lodged. The taper, which can be provided to be continuous or discrete (in steps), allows the adapter to be used for different cartridges.

In this context, the adapter can be designed according to the invention to be a tube with a circular cross-section. Conceivable materials for the adapter include flexible elastic plastic materials to fix an inserted cartridge in place. The adapter can be firmly connected to the base body or be plugged into a bracketing on the base body. A sleeve or a depression in the base body can be provided as bracketing into which the adapter can be plugged.

According to the invention, the layers can be connected to each other and to the base body through a detachable adhesive or a bonding agent. The variable shaping tool according to the invention can be used to pre-shape a bone cement for insertion of an artificial acetabulum.

Figure 2:
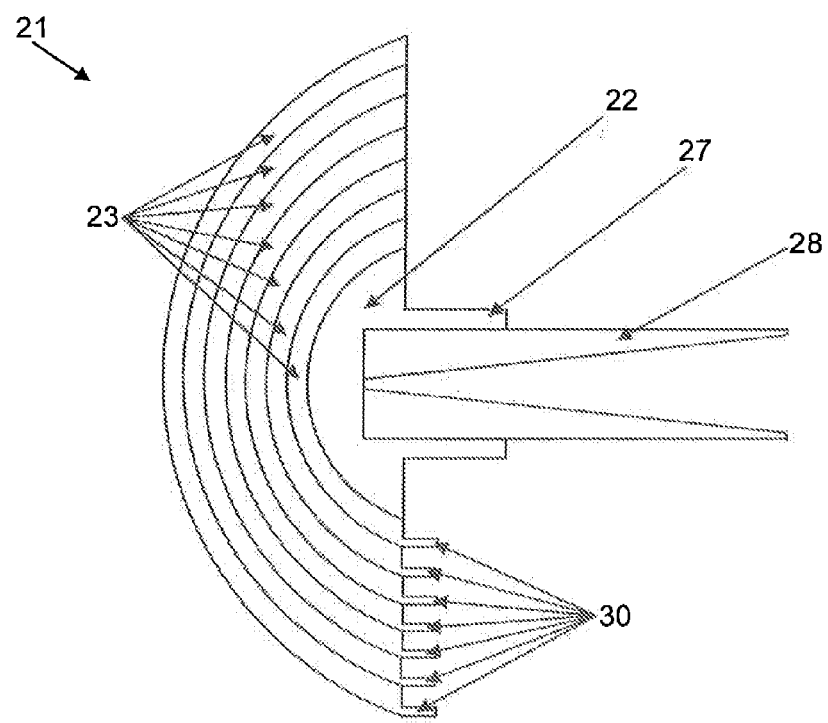
Figure 3:
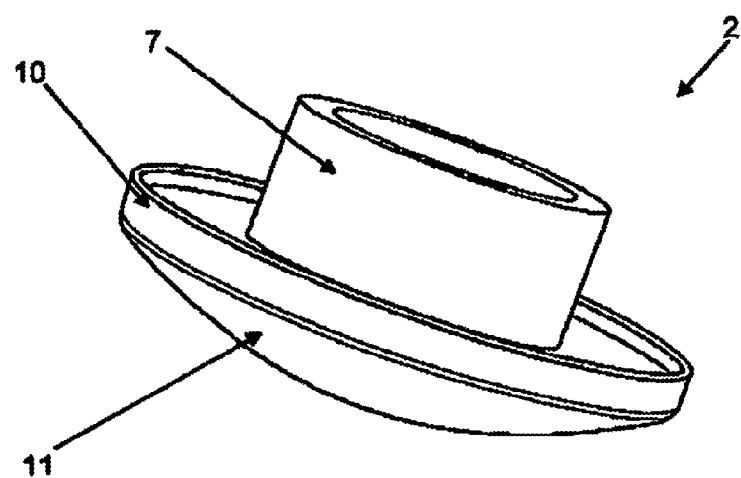
Figure 4:
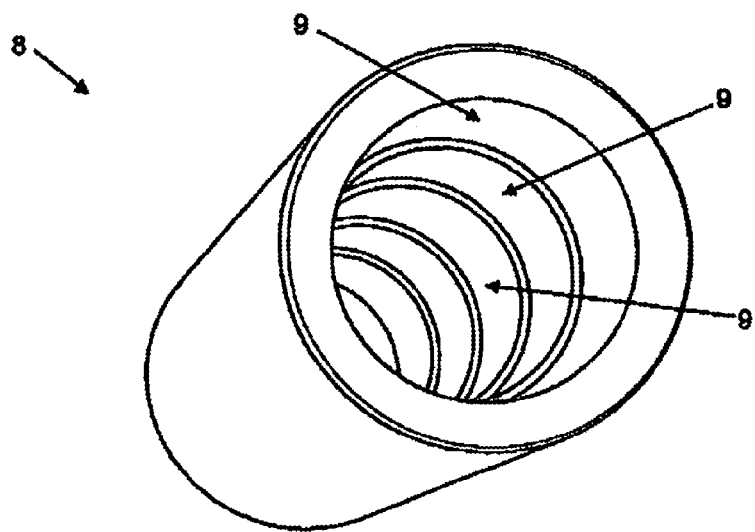
Figure 5:
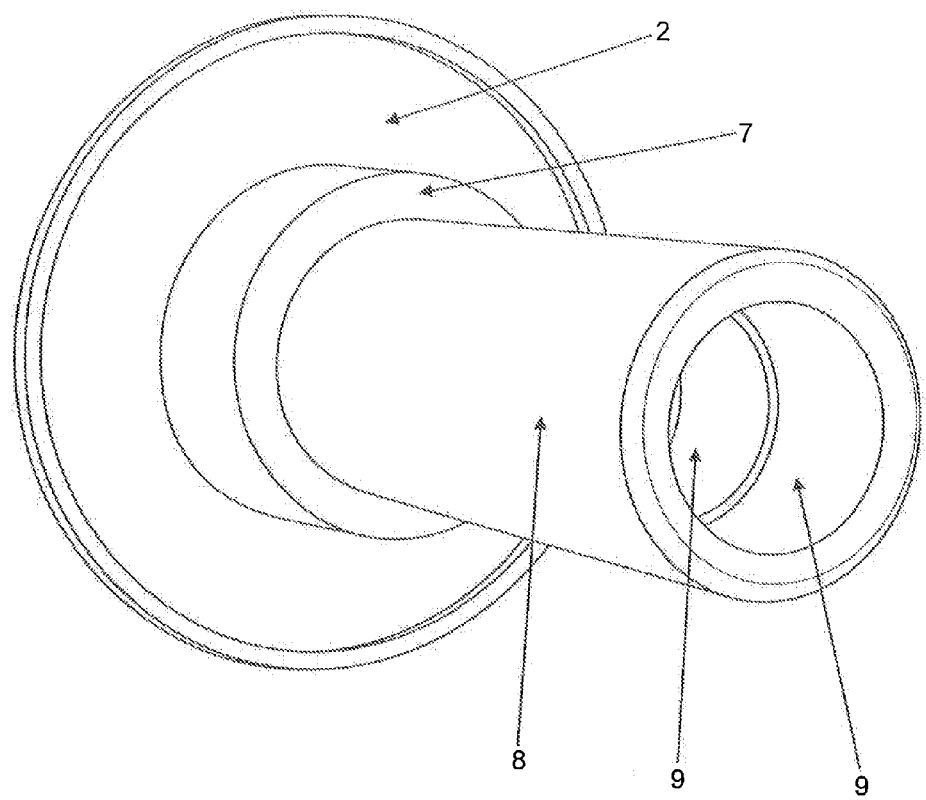
Figure 6:
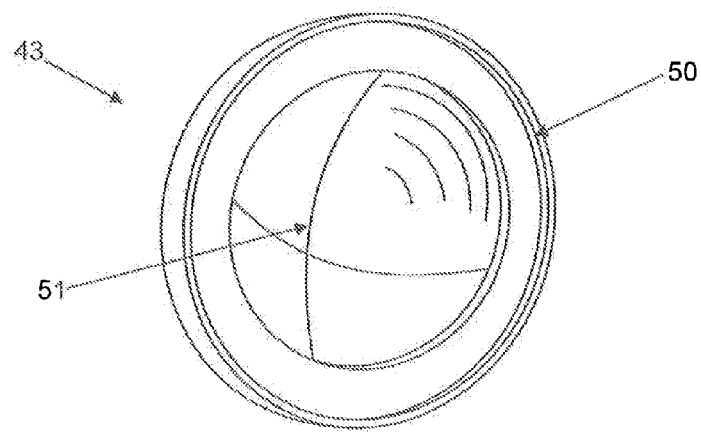

Exemplary embodiments of the invention shall be illustrated in the following on the basis of six schematic figures, though without limiting the scope of the invention. In the figures:

FIG. 1: shows a schematic perspective view of a multi-layered shaping tool according to the invention for shaping a cement layer;

FIG. 2: shows a schematic cross-sectional view of a second multi-layered shaping tool according to the invention for shaping a cement layer;

FIG. 3: shows a schematic perspective view of a base body for a shaping tool according to the invention;

FIG. 4: shows a schematic perspective view of an adapter for a shaping tool according to the invention;

FIG. 5: shows a schematic perspective view of a base body for a shaping tool according to the invention having the adapter inserted; and FIG. 6: shows a schematic perspective view of a detachable layer for a shaping tool according to the invention having a smaller diameter.

FIG. 1 shows a schematic perspective view of a multi-layered shaping tool 1 according to the invention for shaping a bone cement layer. The shaping tool 1 comprises a base body 2 with a level surface that points towards the observer in FIG. 1. On the side of the base body 2 facing away from the observer, the base body 2 has a curvature in the form of a spherical segment that points away from the observer of FIG. 1. The base body 2 is fabricated from a relatively hard plastic material, such as, for example, polyethylene or polypropylene.

The curvature of the base body 2 is fully covered by a first layer 3 that has an even thickness. Likewise, the first layer 3 is fully covered by a second layer 4. The second layer 4 is fully covered by a third layer 5, which in turn is fully covered by a fourth layer 6. The layers, 3, 4, 5, 6, are fabricated from a flexible plastic material, such as, for example, silicone. The layers, 3, 4, 5, 6, adhere to each other and to the base body 2.

A sleeve 7 in the form of a cylindrical tube piece is arranged in central position on the level surface of the base body 2. An adapter 8 in the form of a tube is plugged into the sleeve 7. The internal diameter of the adapter 8 is not constant throughout, but rather tapers in the direction of the base body 2 in discrete steps 9. The internal diameter of the adapter 8 decreases with each step 9 that is situated closer to the base body 2. The internal diameter of the adapter 8 within each step 9 is constant.

Upon bone cement being applied with a cartridge into the cancellous bone of an acetabulum during an operation for insertion of an artificial hip joint, the cartridge or the cartridge tip, which was just used, can be plugged into the adapter 8. A soon as the internal diameter of the adapter 8 matching the cartridge tip is reached, the cartridge or the cartridge tip is firmly lodged in the adapter 8 and can be used as handle for the shaping tool 1.

A matching size of the spherical curvature of the shaping tool 1 is selected and set depending on the size of the artificial acetabulum to be inserted by manually removing all layers 3, 4, 5, 6 that are too large. In order to easily recognise the exact size of layers 3, 4, 5, 6, i.e. the dimensions of the curvatures, a labelling (not shown) can be provided on the flat rear sides of the layers 3, 4, 5, 6 or on the curvatures themselves to indicate the diameter of the corresponding layer 3, 4, 5, 6. Alternatively or in addition, a colour-coding can be used, in which the different sizes of layers 3, 4, 5, 6 are assigned to certain diameters of the curvatures in order to prevent errors during application.

While the base body 2 has a diameter of 45 mm, the first layer 3 has a diameter of 48 mm, the second layer 4 has a diameter of 52 mm, the third layer 5 has a diameter of 58 mm, and the fourth layer has a diameter of 65 mm. The diameter of the base body 2 and of the discs 3, 4, 5, 6 shall be understood to mean the diameter of the largest circle of the spherical segment or of the curvature of the base body 2 or of the discs 3, 4, 5, 6.

The surfaces of layers 3, 4, 5, 6 and base body 2 are smooth to prevent the bone cement from adhering to them. The material of layers 3, 4, 5, 6 and base body 2 must be chemically resistant to the bone cement.

Once the non-matching layers 3, 4, 5, 6 have been removed, i.e., for example, have been pulled off, torn or taken off, the shaping tool 1 can be pressed into the bone cement using the cartridge as a handle in order to not only solidify the bone cement by means of the pressure exerted and to squeeze out undesirable included gas bubbles, but also to pre-shape the bone cement such that the artificial acetabulum can be placed in matching manner on the pre-shaped bone cement. Due to the bone cement shape matching the shape of the artificial acetabulum, few or no air bubbles remain between the bone cement and the artificial acetabulum which might adversely affect the connection of the two and thus the attachment of the artificial joint. Accordingly, the shaping tool 1 is used much like a stamp to shape the cement. A thin cement layer can be shaped in the process.

Said principle can also be generalised to apply to other joints as well, in that the shaping tool 1 can also be used in other operations, in which bone cement is shaped or artificial joints are inserted.

The individual components from which the shaping tool 1 is assembled are shown in FIGS. 3, 4, 5, and 6.

FIG. 2 shows a schematic cross-sectional view of an alternative shaping tool 21 according to the invention. The shaping tool 21 comprises a base body 22 having a curved surface (on the left in FIG. 2) for shaping a cement. The size of the curvature of the base body matches the smallest hip joints or other joints that are encountered. In general, it fits the smallest parts needing to be cemented.

Multiple layers 23 are arranged above the curvature of the base body 22 in an onion skin-like manner. Each of the seven layers 23 increases the diameter of the curvature. This renders each of the layers 23 fitting a certain size of part to be inserted (for example of an artificial acetabulum). The outermost layer 23 corresponds to the largest part to be cemented that may be encountered and/or the largest artificial acetabulum to be inserted.

The base body 22 comprises, in its centre, a depression and a sleeve 27 extending said depression. An adapter 28 is plugged into said depression and sleeve 27 and serves for attachment of a handle, cartridge or cartridge tip. The internal diameter of the adapter 28 tapers towards the base body 22. The adapter is fabricated from a deformable while elastic material such that the plugged-in handle or the plugged-in cartridge or cartridge tip is lodged firmly in the adapter. The handle or the cartridge used as handle can be used to use the shaping tool 21 conveniently for shaping a cement.

In order to be able to pull off the layers 23 more easily, or separate them from each other and from the base body 22, a tongue 30 is provided on each layer by means of which the layer 23 can be grasped. Pulling on the tongue 30 allows each layer 23 to be removed conveniently and rapidly in order to provide a shaping tool 21 of matching curvature.

FIG. 3 shows a schematic perspective view of a base body 2 for a shaping tool according to the invention. The base body 2 has, on its flat side, a cylindrical sleeve 7 into which a handle or adapter can be plugged. The base body 2 has a circumferential rigid cylindrical tongue 10 which, if designed appropriately, serves to keep layers arranged above it better on the base body 2. FIG. 3 clearly shows the curvature 11 of the base body 2 which can be pressed into the liquid cement for placing an impression in the cement.

FIG. 4 shows a schematic perspective view of a tube-shaped adapter 8 having a cylindrical external jacket that is suitable to be inserted into the sleeve 7 of the base body 2 according to FIG. 3. Five steps 9 can be seen to be situated inside the adapter 8. Each of the steps 9 effects the adapter 8 to have a smaller diameter towards one side. The adapter 8 allows different cartridges and handles differing in dimensions to be used as handle for a shaping tool according to the invention. Using a cartridge as handle, the size of the cartridge ensures that the shaping tool according to the invention can be handled both with ease and forcefully. Moreover, the shaping tool itself can be designed to have smaller dimensions such that space can be saved during storage and the shaping tool is less expensive to manufacture.

FIG. 5 shows a schematic perspective view of a base body 2 for a shaping tool according to the invention having the adapter 8 inserted. The cylindrical external shape of the adapter 8 exactly fits in the sleeve 7 of the base body 2 such that the adapter is plugged into the sleeve 7 in a press-fit manner. The adapter 8 was plugged into the sleeve 7 in a manner such that step 9 with the largest diameter faces away from the base body (pointing out of the plane of the drawing in FIG. 5).

FIG. 6 shows a schematic perspective view of a curved layer 43 that can be arranged on the curved surface of a base body (such as is shown, for example, in FIG. 3) of a shaping tool according to the invention. The layer 43 has a flexible circumferential tongue 50 on its rim that can be used to pull the layer 43 off another layer or off the base body upon which it resides. The curvature 51 of the layer 43 is indicated in FIG. 6 through lines on the inside of the curved layer, which only serve for illustrative purposes without any further meaning. The bulge of the curvature extends into the plane of the drawing in FIG. 6.

The features of the invention disclosed in the preceding description and in the claims, figures, and exemplary embodiments, can be essential for the implementation of the various embodiments of the invention both alone and in any combination.

LIST OF REFERENCE NUMBERS

1, 21 Shaping tool
2, 22 Base body
3, 23, 43 Layer
4, 5, 6 Layer
7, 27 Sleeve
8, 28 Adapter
9 Step
10, 30, 50 Tongue
11, 51 Curvature

The invention claimed is:

1. A shaping tool for shaping a smooth bone cement surface for implantation of an artificial acetabulum, the shaping tool comprises a curved base body having a first side comprising an outer curved surface and a second side, located opposite with respect to the first side of the curved base body, comprising a flat surface, wherein a sleeve extends outwardly away from the flat surface of the second side of the curved base body, wherein the shaping tool further comprises a first layer covering the outer curved surface of the curved base body and connected to the curved base body in a detachable manner, and at least one second layer covering the first layer and connected to the first layer in a detachable manner, and further wherein the outer curved surface of the curved base body is continuous and uninterrupted.

2. The shaping tool according to claim 1, further comprising three to forty second layers, which cover each other, at least in part, in the manner of onion skins, and are connected to each other in a detachable manner.

3. The shaping tool according to claim 1, wherein the outer curved surface of the curved base body is a spherical segment.

4. The shaping tool according to claim 1, wherein the shaping tool further comprises a handle or an adapter, wherein the handle or the adapter is a tube that tapers on its inside in one direction.

5. The shaping tool according to claim 4, wherein the handle or the adapter is a tube-shaped adapter that tapers in discrete steps.

6. The shaping tool according to claim 4, wherein the adapter or the handle is pluggable into at least one selected from the curved base body, a depression in the second side of the curved base body and the sleeve on second side of the curved base body.

7. The shaping tool according to claim 1, wherein the outer curved surface of the curved base body has a diameter of 35 to 50 mm.

8. The shaping tool according to claim 1, wherein a thickness of each layer of the layers is between 0.5 and 15 mm.

9. The shaping tool according to claim 1, wherein a tongue is arranged on each layer that is configured to allow the corresponding layer along with all layers arranged above the corresponding layer to be manually detachable from at least one selected from the layers arranged below the corresponding layer and the curved base body, by pulling or lifting the corresponding layer off.

10. The shaping tool according to claim 1, wherein the first and second layers are connected to the curved base body and to each other in a manually detachable manner.

11. The shaping tool according to claim 1, wherein a labelling is arranged on at least one of the layers and on the curved base body, wherein the labelling allows a diameter of the curved surface of the base body to be read such that a certain size of an artificial acetabulum is allocatable to each layer.

12. The shaping tool according to claim 1, wherein the first and second layers are situated in a positive fit within each other and on the curved base body.

13. The shaping tool according to claim 1, wherein the first and second layers consist of a hard material or of a soft material.

14. The shaping tool according to claim 1, wherein curved surfaces of the curved base body and the first and second layers are smooth.

15. The shaping tool according to claim 1, wherein the curved base body and the first and second layers are constructed of materials that are destructible by exposure to steam.

16. A shaping tool for shaping a smooth bone cement surface for implantation of an artificial acetabulum, the shaping tool comprises a curved base body having a first side comprising a curved surface and a second side, located opposite with respect to the first side of the curved base body, comprising a flat surface, wherein a sleeve extends outwardly away from the flat surface of the second side of the curved base body, wherein the shaping tool further comprises a first layer covering the curved surface of the curved base body and connected to the curved base body in a detachable manner, and at least one second layer covering the first layer and connected to the first layer in a detachable manner, wherein the curved base body comprises a circumferential rigid cylindrical tongue.

17. A shaping tool for shaping a smooth bone cement surface for implantation of an artificial acetabulum, the shaping tool comprises a curved base body having a first side comprising an outer curved surface and a second side, located opposite with respect to the first side of the curved base body, comprising an outwardly-facing flat surface, wherein a sleeve extends outwardly away from the outwardly-facing flat surface of the second side of the curved base body, wherein the shaping tool further comprises a first layer covering the curved surface of the curved base body and connected to the curved base body in a detachable manner, and at least one additional layer covering the first layer and connected to the first layer in a detachable manner, and further wherein at least one flat edge of the at least one additional layer, located at an outermost circumference of the at least one additional layer, comprises a bottom-most surface that does not extend beyond a plane defined by the outwardly-facing flat surface of the curved base body.

18. A shaping tool for shaping a smooth bone cement surface for implantation of an artificial acetabulum, the shaping tool comprises a curved base body having an outermost circumference, a first side comprising a curved surface and a second side, located opposite with respect to the first side of the curved base body, comprising a flat surface, wherein a sleeve extends outwardly away from the flat surface of the second side of the curved base body, wherein the shaping tool further comprises a first layer covering the curved surface of the curved base body and connected to the curved base body in a detachable manner, and at least one second layer covering the first layer and connected to the first layer in a detachable manner, and further wherein the flat surface of the curved base body extending from the sleeve of the curved base body to the outermost circumference of the curved base body is continuous and uninterrupted.

* * * * *